United States Patent
Bradbury et al.

(10) Patent No.: US 12,254,988 B2
(45) Date of Patent: Mar. 18, 2025

(54) SYSTEM FOR AN EPIDEMIOLOGICAL APPROACH TO MUSCULOSKELETAL RISK DETERMINATION AND PREDICTION OF ERGONOMIC RISKS, PHYSICAL DEMAND PERFORMANCE LEVELS, OCCUPATIONAL HEALTH MONITORING AND ENVIRONMENTAL, HEALTH, SAFETY AND SUSTAINABILITY MODELING

(71) Applicants: Samuel Bradbury, Santa Fe, NM (US); Mark Heidebrecht, Olathe, KS (US)

(72) Inventors: Samuel Bradbury, Santa Fe, NM (US); Mark Heidebrecht, Olathe, KS (US)

(73) Assignee: Ergonomics International LLC, Olathe, KS (US)

( * ) Notice: Subject to any disclaimer, the term of this patent is extended or adjusted under 35 U.S.C. 154(b) by 921 days.

(21) Appl. No.: 17/240,061

(22) Filed: Apr. 26, 2021

(65) Prior Publication Data
US 2021/0241919 A1    Aug. 5, 2021

Related U.S. Application Data

(63) Continuation-in-part of application No. 15/871,810, filed on Jan. 15, 2018, now Pat. No. 11,023,841.

(60) Provisional application No. 63/019,099, filed on May 1, 2020, provisional application No. 63/015,532, filed on Apr. 25, 2020, provisional application No. 62/446,843, filed on Jan. 17, 2017.

(51) Int. Cl.
*G16H 50/30* (2018.01)
*G06K 19/06* (2006.01)
*G06Q 10/0635* (2023.01)

(52) U.S. Cl.
CPC ....... *G16H 50/30* (2018.01); *G06K 19/06037* (2013.01); *G06Q 10/0635* (2013.01)

(58) Field of Classification Search
CPC ........ G16H 50/30; G16H 15/00; G16H 30/20; G16H 40/67; G16H 50/80; G06K 19/06037; G06Q 10/0635; G06Q 10/0631; G06Q 10/0637
See application file for complete search history.

(56) References Cited

U.S. PATENT DOCUMENTS

| | | | |
|---|---|---|---|
| 8,370,170 B2* | 2/2013 | Legge | A63B 24/0062 434/117 |
| 11,328,239 B2* | 5/2022 | Baek | G06V 40/23 |
| 2010/0094645 A1* | 4/2010 | Carroll | G16H 20/30 705/2 |
| 2020/0000414 A1* | 1/2020 | McCord | A61B 5/1114 |

FOREIGN PATENT DOCUMENTS

CN         104200310      * 12/2014    ......... G06Q 10/06

* cited by examiner

*Primary Examiner* — Tom Y Lu
(74) *Attorney, Agent, or Firm* — My Patent Guys; Christopher Pilling

(57) ABSTRACT

A worksite risk analysis and documentation system and method defines, captures, categorizing, and documents, while analyzing functional physical demands of a plurality of jobs, tasks, body movements to provide musculoskeletal and health and safety risks at various worksites. The system uses the use of odds ratios in the determination of risk for musculoskeletal, ergonomic and EHS&S risk factors. A built in QR tracking system for Covid-19 is provided.

17 Claims, 17 Drawing Sheets

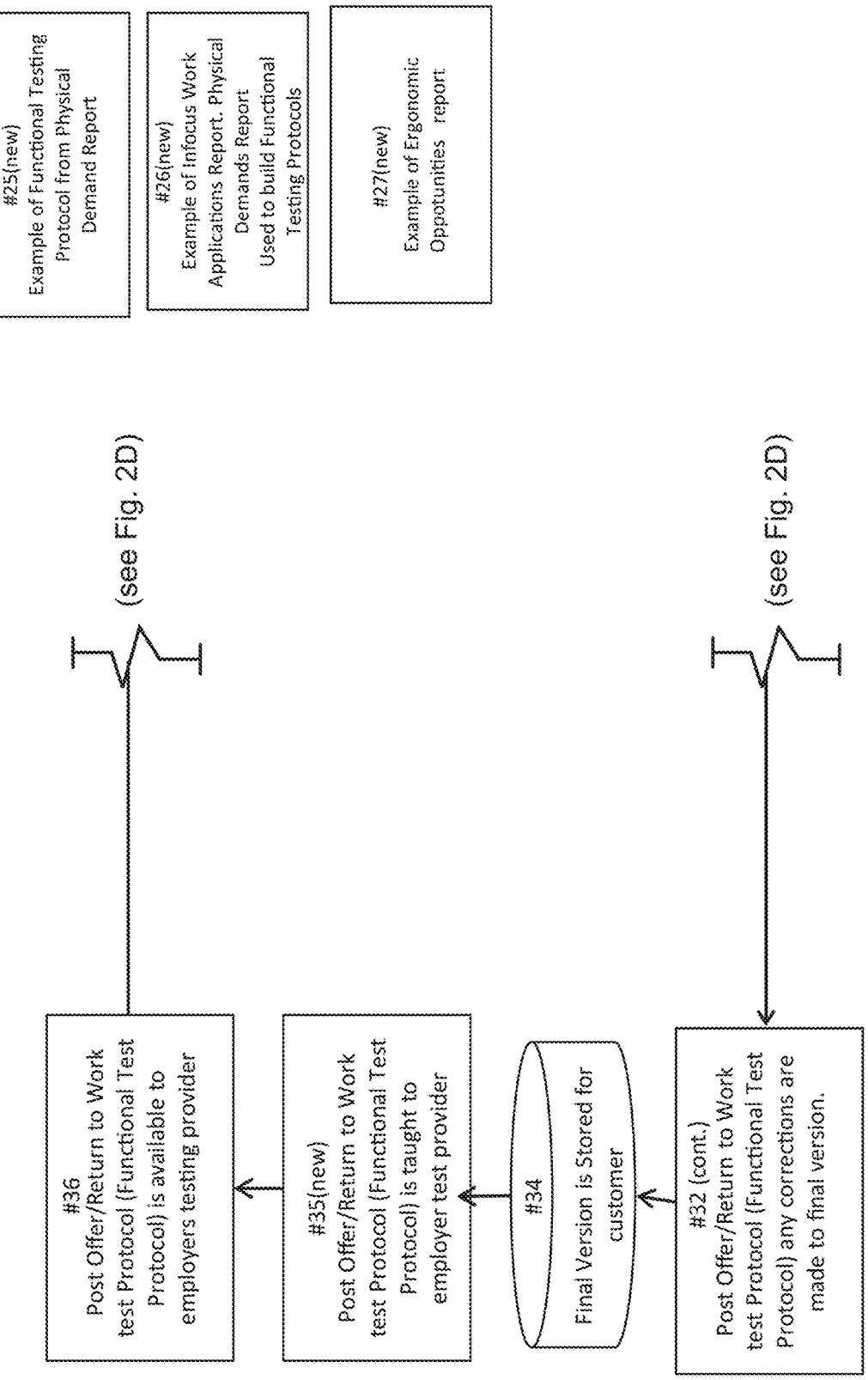

SYSTEM FOR AN EPIDEMIOLOGICAL APPROACH TO MUSCULOSKELETAL RISK DETERMINATION AND PREDICTION OF ERGONOMIC RISKS, PHYSICAL DEMAND PERFORMANCE LEVELS, OCCUPATIONAL HEALTH MONITORING AND ENVIRONMENTAL, HEALTH, SAFETY AND SUSTAINABILITY MODELING

CROSS-REFERENCE TO RELATED APPLICATIONS

The present application claims priority to U.S. Provisional Application Ser. No. 63/015,532 filed on Apr. 25, 2020 and 63/019,099 filed on May 1, 2020 both entitled "AN EPIDEMIOLOGICAL APPROACH TO ERGONOMIC AND MUSCULOSKELETAL RISK CALCULATION AND PREDICTION", and is a Continuation-in-Part Application to U.S. Nonprovisional application Ser. No. 15/871,810 filed on Jan. 15, 2018 entitled "WORKSITE RISK ANALYSIS AND DOCUMENTATION SYSTEM AND METHOD" which claims priority to U.S. Provisional Application Ser. No. 62/446,843 filed on Jan. 17, 2017 entitled "A VIDEO BASED VISUAL WORKSITE ANALYSIS DOCUMENTATION SYSTEM," the disclosures of which are hereby incorporated in their entirety at least by reference.

BACKGROUND OF THE INVENTION

1. Field of the Invention

The present invention generally relates to health and safety and more particularly to a system for an epidemiological approach to musculoskeletal risk determination and prediction of ergonomic risks, physical demand performance levels, occupational health monitoring and environmental, health, safety & sustainability (EHS&S) modeling.

2. Description of Related Art

Health and safety are primary concerns for companies relating to worksite tasks performed by company employees. Further, the majority of worksite injuries are associated with exposure to ergonomic risk factors. Thus, calculating risks and opportunities relating to specific job tasks are critical, and documenting the system is paramount. Further, there are improvements needed in this field. Consequently, a system for an epidemiological approach to musculoskeletal risk determination and prediction of ergonomic risks, physical demand performance levels, occupational health monitoring and EHS&S modeling.

BRIEF SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Advantageously, it is an object of the present invention to provide the following features: (a) the use of odds ratios in the determination of risk for musculoskeletal, ergonomic and EHS&S risk factors; (b) the use of video capture in the development of evidence based and standardized physical demand reports of jobs; (c) the determination of the levels of risk factor determined using the odds ratio methods via logic calculations; (d) the integration and cross validation of standardized ergonomic risk assessment tools with the odds ratio determinations by a plurality of body parts; (e) the integration of Fatigue Ratio and Fatigue Systems to improve accurate work rest ratio and worker recovery calculations; (f) a built in QR tracking system for Covid-19, cleaning, JSAs, LOTO, and inspections as well as customizable QR coding activities; (g) the integration of solutions data base to aid in determining appropriate mitigation solutions based on risks determined using odds ratio calculations; and, (h) logic and methods including drop and drag card format for the development of an effective job cycle outline for a job, day, or week, which is specific to the integration of active time, non-active time, breaks, and batch changes.

It is a further object of the present invention to provide the following features: (a) Evidence Based Risk Development using a library of standardized definitions, epidemiological modeling, and global standards to provide a foundation of empirical and objective formulations; (b) the integration of physical demands of jobs, ergonomic risk analysis, human factors error criteria and EHS&S surveys; (c) the inclusion of occupational health tracking from date of initial report and potential relationship with epidemiological risk factors; and, (d) the inclusion of EHS&S modeling to reduce early warning musculoskeletal concerns.

In order to do so a system is provided, the system comprising an Internet-connected computerized appliance having a processor and coupled to a data repository, the processor executing software from a non-transitory storage medium, the software providing an interactive health monitoring and musculoskeletal risk determination and prediction system, the system enabling a user to: log on; input data related to one or more body parts; capture and store media data to document physical demands and ergonomic risk corresponding to a plurality of tasks at a worksite; calculate and determine musculoskeletal and ergonomic risk factors based on the inputted data; utilize an odds ratio database in the calculation and determination of the musculoskeletal and ergonomic risk factors; analyze the musculoskeletal and ergonomic risk factors; and, generate a plurality of reports detailing and illustrating the musculoskeletal and ergonomic risk factors.

In one embodiment, the input data related to one or more body parts further comprises body movement tasks, lifting movements, push movements, and pull movements. In one embodiment, the worksite is a home office. In one embodiment, the system provides the integration and cross validation of standardized ergonomic risk assessment tools with the odds ratio data from the odds ratio database. In another embodiment, wherein the system provides the integration of fatigue ratio and fatigue systems to improve calculations of the musculoskeletal and ergonomic risk factors. In another embodiment, the system provides a QR code tracking and monitoring system for occupational health and safety. In another embodiment, wherein the QR code tracking and monitoring system comprises Covid-19 data tracking, wherein the data tracking essentially consists of: temperature tracking, quarantine tracking, remote data entry, and cleaning monitoring. In another embodiment, wherein the QR code tracking and monitoring system wherein the occupational health and safety comprises job safety analysis, LOTO data, and customizable QR coding activities. In another embodiment, wherein the odds ratio data base integrates a solutions database to aid in calculations. In one embodiment, the system further enables a user to: input additional data in a self-assessment module for ergonomic risk tracking. In another embodiment, the system further enables a user to: drop and drag date specific task lists for the development of an effective job cycle for a period of time. In one embodiment, the analysis of the musculoskeletal and ergonomic risk factors is via sliding bars to visually analyze the data to determine which components of lifting movements are creating the highest risk. In one embodiment, the system further enabling the user to: identity specific body parts affected by the physical demands. In another embodiment, the system further enabling the user to: create a body part based risk report based on potential injury cost.

In another aspect of the invention, a method is provided, comprising steps: (a) providing training and credentialing of a plurality of users for use of a worksite risk analysis and documentation system; (b) enabling a user of the plurality of users to access the worksite risk analysis and documentation system from a geographical location via an Internet connection; (c) capturing media data at a worksite, wherein the media data includes video or images documenting physical demands and ergonomic risk of the user or an additional user; (d) capturing input data related to one or more body parts; (e) storing the inputted data and captured media data plurality of images in non-transitory storage medium; (f) calculating musculoskeletal and ergonomic risk factors based on the inputted data and captured media data; (g) analyzing the musculoskeletal and ergonomic risk factors; and, (h) generating a plurality of reports detailing and illustrating the musculoskeletal and ergonomic risk factors.

In one embodiment, the input data related to one or more body parts further comprises body movement tasks, lifting movements, push movements, and pull movements.

The foregoing has outlined rather broadly the more pertinent and important features of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present disclosure. It should be realized by those skilled in the art that such equivalent structures do not depart from the spirit and scope of the invention as set forth in the appended claims

BRIEF DESCRIPTION OF THE SEVERAL VIEWS OF THE DRAWINGS

Other features and advantages of the present invention will become apparent when the following detailed description is read in conjunction with the accompanying drawings, in which:

FIGS. 2A-E is a flow diagram for the system according to an embodiment of the present invention.

FIG. 3 is an exemplary user interface for inputting data according to an embodiment of the present invention.

FIG. 6 shows a custom Odds Ratio epidemiological database according to an embodiment of the present invention.

FIG. 11 shows an exemplary instance of COVID-19 monitoring according to an embodiment of the present invention.

FIG. 12 shows an exemplary user interface of the system enabling self-assessment for ergonomic risk tracking according to an embodiment of the present invention.

DETAILED DESCRIPTION OF THE PREFERRED EMBODIMENT

Figure 1:
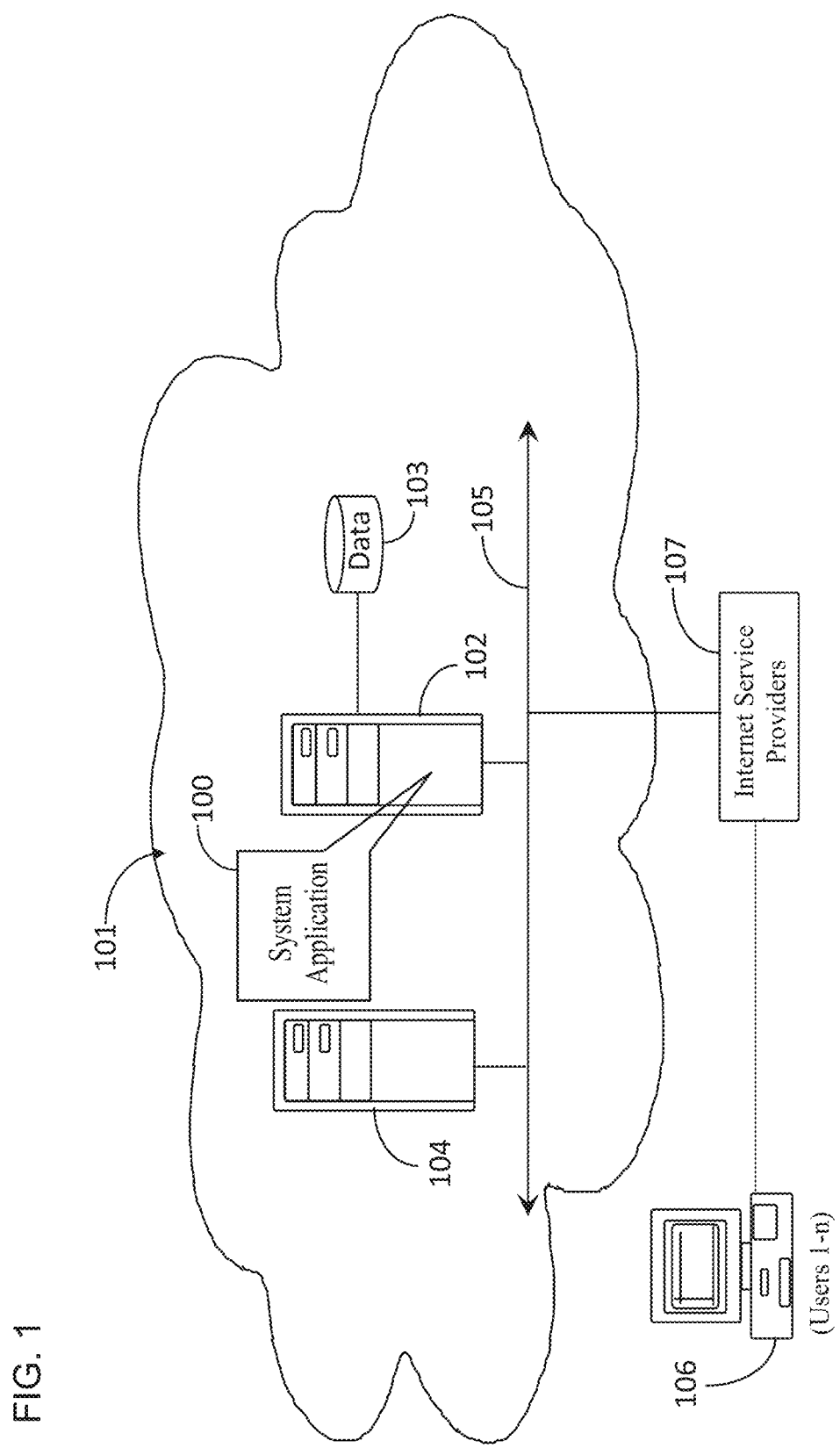
FIG. 1 is an architectural diagram of an Internet computer network system according to an embodiment of the present invention.
Figure 2A:
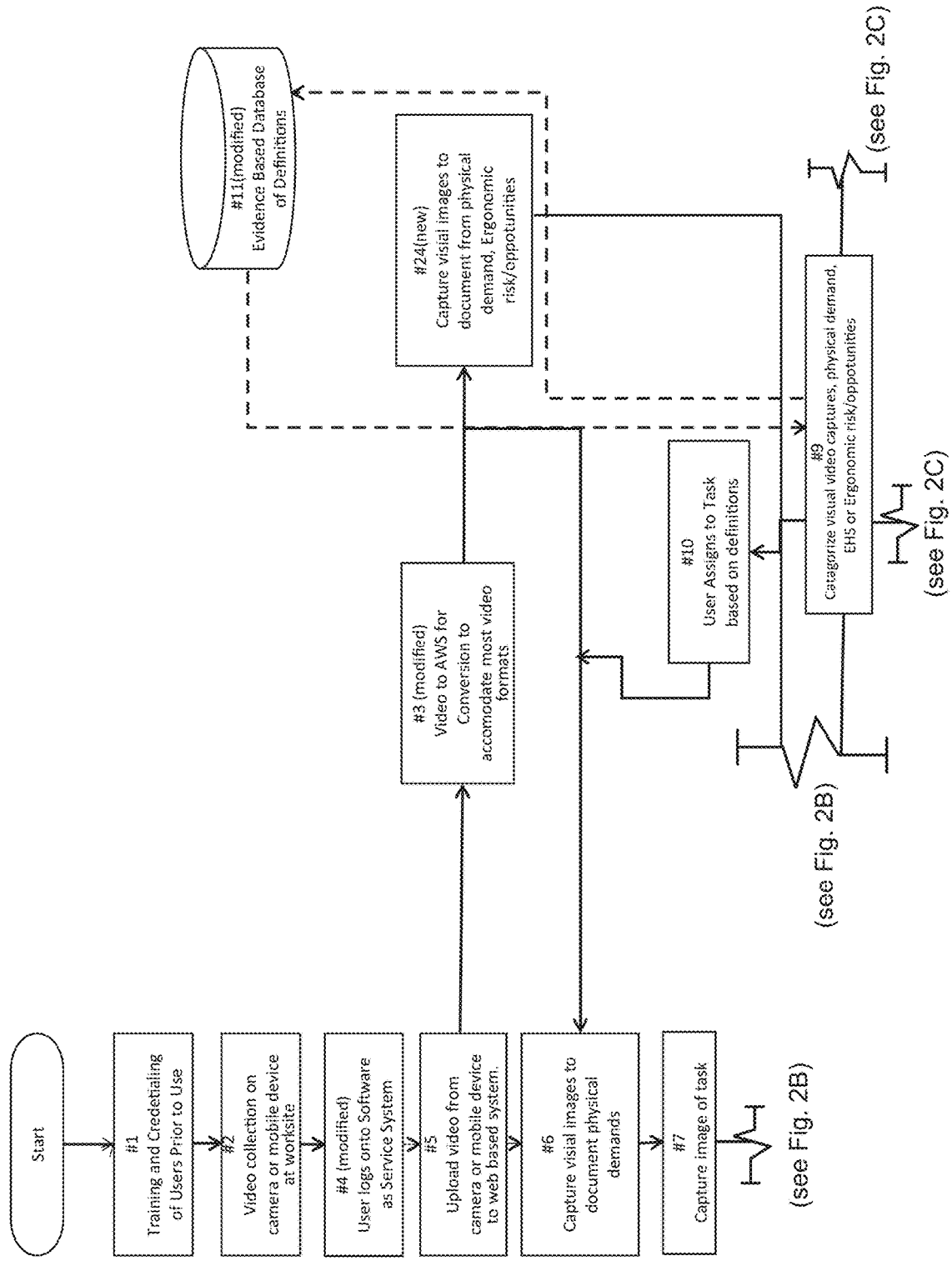
Figure 2B:
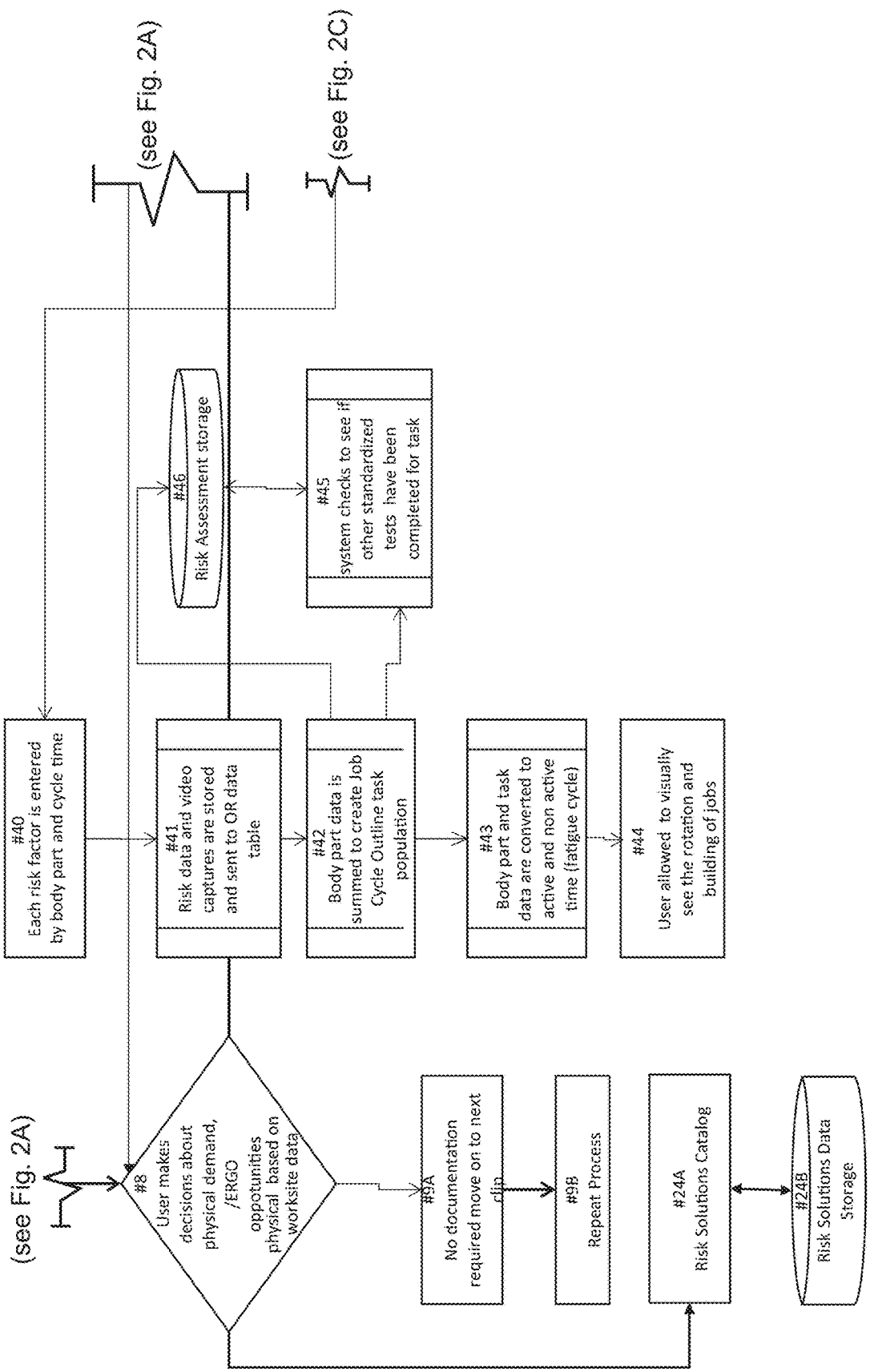
Figure 2C:
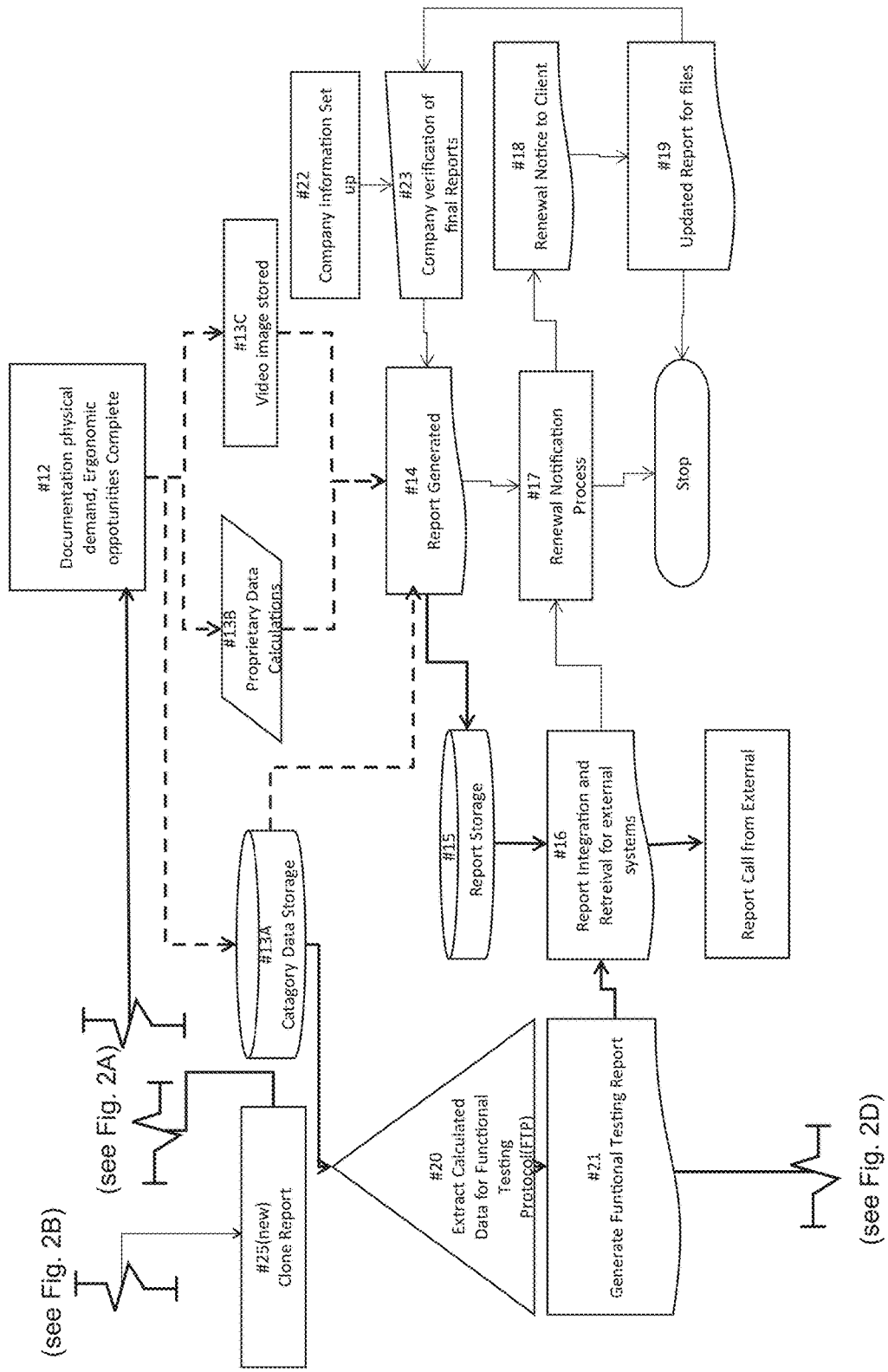
Figure 2D:
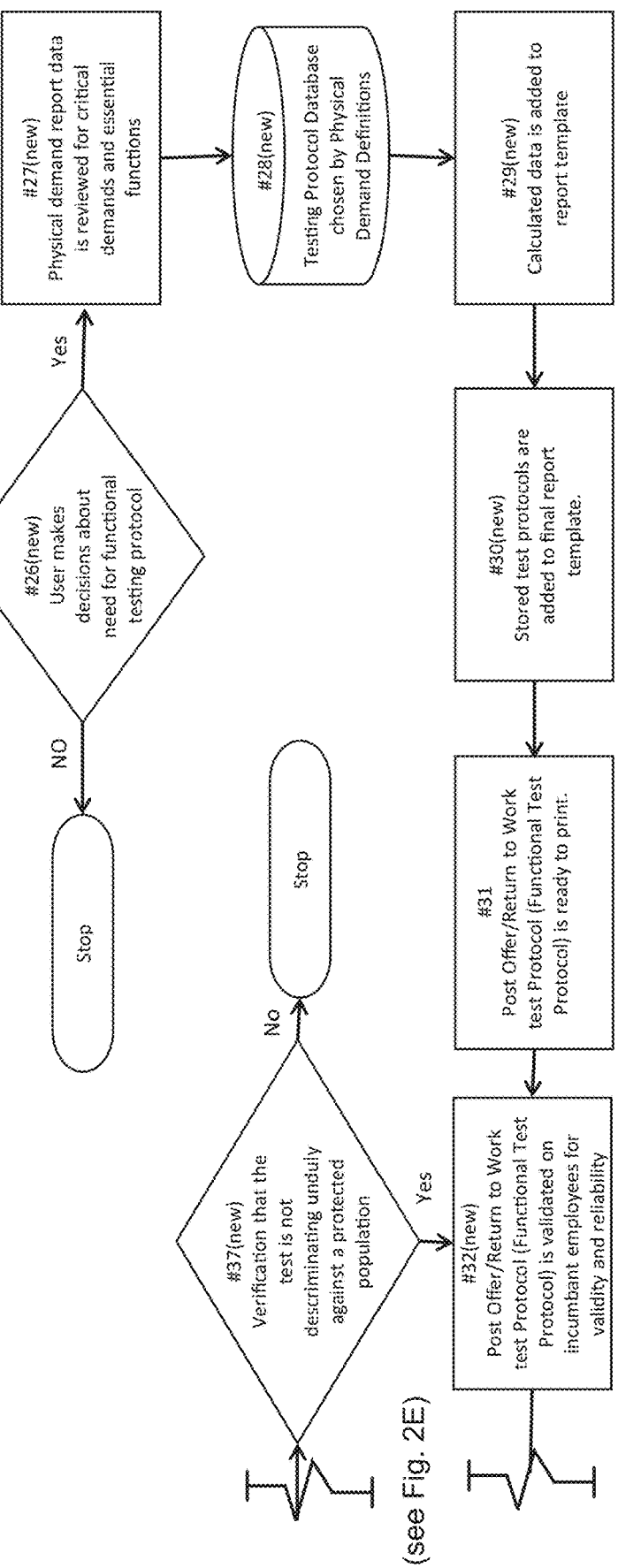

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein to specifically provide a worksite risk analysis and documentation system and method.

The word "a" is defined to mean "at least one." The terminology includes the words above specifically mentioned, derivatives thereof, and words of similar import. "Worksite" and "workplace" may be used interchangeably herein, and is defined as a place (such as a shop, factory, office, home, or area of land) where work is done, performed, completed, built, or assembled by workers.

In one embodiment, the system and method defines captures, categorizing, and documents, while analyzing functional physical demands of a plurality of jobs at various worksites, including environmental health and safety, health, and ergonomic risks.

In one embodiment, the system allows a user to perform the following tasks: define functional physical demands associated with specific job tasks using evidence based definitions, upload video data from camera or mobile devices, visually display and capture worksite images from video data, visually document task based essential functions and physical demands for the development of task specific functional testing protocols, visually document EHS risks and opportunities through visual and pdf export, determine Dictionary of Occupational Title Work Levels by proprietary calculations, manage multiple physical demands of the same type e.g. multiple reaches or lifts, calculate Dictionary of Occupational Title work defined levels, calculate Ergonomic Risk Components by Job Task, calculate EHS Risk Components by Job Task, integrate the system with Functional Capacity Assessment Software System, provide evidenced based definitions of physical demands of work, produce image based reports, provide report revision protection, clone reports and store for future uses and integrations, store images for reporting, and access assess the system on the Internet.

In another embodiment, the system allows a user to perform the following tasks and features: (a) Use of Odd Ratio Calculations for determining the ergonomic and musculoskeletal risk of injury; (b) Use of Odds Ratio Composites for determining the ergonomic and musculoskeletal risk of injury by body part; (c) Use of internal database of articles and odds ratio data from peer-reviewed references to establish odds ratios for musculoskeletal exposures; (d) Use of calculation logic of recovery time within a task or work cycle to determine musculoskeletal exposure; (e) Use of medically established odds ratio logic to determine what truly constitutes a musculoskeletal risk (an OR>2); (f) Use of quartile ranging to segment risk into user-friendly striations for graded risks; (g) Use of specifically referenced odds ratio risk numbers and scores for determining risks related to manual material handling tasks; (h) Use of specifically referenced odds ratio risk numbers and scores for determining risks related to whole-body vibration risk; (i) Use of specifically referenced odds ratio risk numbers and scores for determining risks related to hand-arm vibration risk; (j) Use of specifically referenced odds ratio risk numbers and scores for determining risks associated with duration of exposure to determine the risk of age-based populations; (k) Calculating "Dollars at Risk" based on normative tables or based on company previous injury dollar exposures, including a company database of injury data based on musculoskeletal injuries and the past three-year associated costs; (l) Calculating "Days at Risk" based on normative tables or based on company previous injury severity rate exposures, including a company database of injury data based on musculoskeletal injuries and the past three-year associated costs; (m) Calculating "Dollars at Risk by Body Part" based on normative tables or based on company previous injury severity exposures and uses this same calculation to create a severity rate by body part; (n) Use of radar graphics to depict ergonomic risk by body parts and risk factors; (o) Use of illustrations that have been commissioned and owned by Ergonomics International, LLC for all testing illustrations including standardized assessment processes; (p) Embedded mitigation library of solutions (Solutions Center) and vendors that are calculated based on the risk score by body part and risk factors; and, (q) Integration of Rstudio as a statistical motor for compiling odds ratio data, wherein RStudio is an integrated development environment for R, a programming language for statistical computing and graphics. Interfaces with the system from AWS servers to perform: composite body part odds ratio score—using the same risk factors from multiple studies to provide a more finite odds ratio for a specific body part, composite risk factor odds ratio score—using similar risk factors from multiple studies to provide a more finite odds ratio for a specific risk factor, composite risk score for multiple at-risk body parts, summary risk scores for all body parts, and summary risk scores for all risk factors.

FIG. 1 is an architectural diagram of an Internet 101 computer network system according to an embodiment of the present invention. The Internet-connected system comprises one or more Internet-connected servers 102 executing the present invention system 100 software from non-transitory media. Server 102 is connected to a data repository 103, which may be any sort of data storage known in the art. The system further comprises a third party Internet-connected server 104 connected to Internet backbone 105. Although one third party Internet-connected server 104 is shown, it is understood that potentially millions of other similar servers are connected to the Internet via Internet backbone 105. A number of users (1-n) 106 are connected to the Internet-connected server via an Internet service provider (ISP) 107, allowing users 106 to access the worksite risk analysis and documentation system.

FIGS. 2A-E is a flow diagram for a system and method according to an embodiment of the present invention. Referring to now to FIGS. 2A-E, the method using the present invention is provided. In step 1, the training and credentialing of users for use of the system is provided. This is critical to maintaining and standardizing the method steps or process of the system. The training environment can vary, for instance, in one embodiment training is in a class room setting, typically over two full days, wherein the users are provided learning materials of the system. In another embodiment, the training is completed online and on demand at the user's pace. Credentialing is required to insure users are qualified to perform various tasks, including but not limited to assessments which are annually renewed. In one embodiment, a user's credential is annually renewed to prove capabilities and knowledge of the system to maintain credential status. In one embodiment, a user's credential status is subject to an annual review of reports the user completed over the previous year. In one embodiment, the training and credentialing is assessed with various testing methods as well known in the art including minimum scores to pass the training program. In another embodiment, users are required to use the system application 100 to complete the reports. Step 1 is critical, as without specific and explicit training in the details of the system and method, the system loses validity and reliability.

In step 2, video data is recorded via a camera or a mobile device at a worksite. The video data provides the foundation of worksite risk analysis and documentation system and method. In one embodiment, an evaluator records a video displaying at least one of a physical demand required by a worker, an ergonomic concern involving a worker, and an environmental health and safety concern involving a worker. In one embodiment, the video data can be recorded on any video camera or mobile device. The video data provides the opportunities which are evaluated, analyzed, and mitigated by the method described herein. This is a particular advantage of the present invention as it provides a consistent and standardized process for which employers can measure, collect, visually document, report, store, and recall data which has previously been done on paper or in spreadsheets in the systems found in the prior art.

In step 4, a user logs into the system 100. The system architecture will be explained in further detail below. The log-in portal of the system allows for a single point of entry into the system, which provides security measures for system. In one embodiment, the system logs entry of any user that accesses the system users, while establishing the location of data in the system based on specific user and company in which the user is affiliated. In another embodiment, the system allows for annual renewal tracking of users and allows for integration of report cloning features. In one embodiment, security measures are required when accessing the system, such as usernames, passwords, and other security tokens as well known in the art, only allowing trained and qualified user access to the system while preventing unauthorized access.

In step 5, the video data is uploaded to the system 100. This is the initial step required for all reporting, documentation, calculations, and analysis of the physical demands, ergonomic concerns, and environmental health and safety (EHS) concerns as previously described. In this step, the user can also isolate each demand, concern, risk, or opportunity into separation documentation files. In one embodiment, the system allows the user to view and manage video data on a single screen. In one embodiment, the system allows image capture that is linked to either an opportunity or physical demand. Further, the system allows for the use of a single image for multiple opportunities or physical demands without leaving the initial captured image. It is a particular advantage of the present invention, that the system allows the user to move through the video data on the screen capturing as many individual and uniquely identified images associated with the physical demands or opportunities noted in the workplace. It is important to note that the video data at this point of the process. This provides security to companies and users within the system in that actual video footage is only used for the capturing of images rather than storing complete video. Images are stored after user has defined and saves them to a data repository 103 on server 102 (FIG. 1).

In step 3, the video data may be converted from various camera formats, allowing end users flexibility in devices that can be used. This provides options for mobile users to collect on the fly and convert, insuring compatibility to current and future formats. This step is only performed if required. In one embodiment, a file converter is used for Apple devices, to convert from Apple formats to PC compatible file types if necessary as well known in the art. The object is to provide consistency and a standardized format. In some embodiments, this process has now been incorporated into the software by uploading to AWS for conversions. Thus all video formats are compatible for the web based software application system 100.

In step 6 or 24 depending on the concern, the visual images are captured and documented to analyze physical demand, ergonomic risk/opportunities. Specifically, in step 6, ergonomic risk factors are used to create an ergonomic risk opportunity list. In one embodiment, the ergonomic risk opportunity list includes a priority ranking for each observation/visual image, a description of the opportunity/risk, and a recommendation to improve the opportunity risk. In Isolate and link opportunities and physical demands using drop down commands on the screens. These dropdowns identify specific physical demands, EHS opportunities, and ergonomic opportunities. Specifics of these identifiers are determined by the research, industry standards and defined definitions provided within the system. Essentially, a user is able to pull a specific image from a video clip taken to visually document the physical demand, EHS opportunity, and ergonomic opportunity and then provide details associated with that image for later calculations and reporting processes.

In step 24, ergonomic risk factors and opportunities and physical demand captured images are isolated via dropdown commands. These dropdowns identify specific body parts affected by physical demand, exposure, and the number of person affected by the risk. The system then calculates, using a programmed dollar amount (customer or data set), a prioritized risk matrix. In one embodiment, the prioritized risk matrix is then linked to a catalogue of solutions including administrative, engineered or personal protective equipment (PPE) which can aid in mitigating the problem. This is advantageous, as In step 7, an image of the task is captured. Specifically, a user can isolate and link opportunities and physical demands using dropdown commands on the various screens of the system. These dropdowns identify specific physical demands, EHS opportunities, and ergonomic opportunities. Specifics of these identifiers are determined by the research, industry standards and defined definitions provided within the system. This process provides, data storage of single image opportunities in multiple categories from a single user screen and sets of dropdown menus of researched and defined details that will be associated with that image in a visual report. The visual report will be described in further detail below.

In step 8, the user makes a decision about EHS, ergonomic, physical demand, and/or risk/opportunity. At this step, the user also begins deciding what they want to collect from the captured image and how many categories it will apply to. Further, the user defines the type of visual report that will be produced as an outcome. The user identifies the critical initial data that needs to be collected and linked to a specific captured image. In one embodiment, the user identifies dropdown information that needs to be linked with the image. It should be understood that the training as described in step 1 is necessary to perform this step, as the definitions are required to be understood and it requires users to understand the differences between physical demand and ergonomic risk. Further, users are required to know EHS concerns and mitigation strategies.

In step 24A, a list of administrative and engineered solutions are created and pulled from a catalog of solutions, wherein the catalog of solution is based on the captured visual images of ergonomic risk/opportunities. These risk solutions provide end users with immediate ways to fix issues either from administrative and engineered controls. Specifically, by pulling through the catalog of solutions, immediate solutions are available without the need to analyze the risk. In step 24B, the catalog of risk solutions is stored in a data repository, such as a data repository 103 (FIG. 2).

In step 9, the user analyzes the images previously captured from the video date into physical demand, EHS or Ergonomic risk/opportunities. Specifically, the user decides what they want to collect from the captured image and how many categories it will apply to. In one embodiment, the user defines the type of visual report that will be produced as an outcome. The user identifies the critical initial data that needs to be collected and linked to a specific captured image. In one embodiment, the user also identifies dropdown information that needs to be linked with the image. Alternatively, in step 9A, if no documentation is required, in step 9B the process is repeated.

In step 10, the user assigns the previously categorized images in step 9 to a task. Specifically, the user divides the captured images into essential and non-essential functions of a job. In one embodiment, the user creates a process for accommodating physical or cognitive deficits for return to work, ADA (Americans with Disabilities Act) accommodation strategies, risk reduction, or safety issue mitigation. In one embodiment, the division between essential and non-essential functions of a job can be visually reported format for employers, physicians, safety managers, case managers, or legal personnel. The visual clarification of essential and non-essential functions allows for faster decisions on accommodations, mitigation, or prioritization.

In step 11, utilizing the evidence based database of definitions, objectifies, standardizes, and clarifies how the end user categorizes the linked data associated with captured images, resulting in continually improving system of defining the data being used for analysis and visual reports. This is a critical step of the system, as it standardizes the details by every user of the system as well as the standardization of definitions for end users of the visual reports. This is a particular advantage of the present invention, as it's the only system and process to have defined physical demands, environmental conditions, or sensory criteria based on peer reviewed literature. Further, it's the only system to actually calculate DOT levels incorporating work rest criteria as well as the only system to establish work levels based on uploaded video data.

In step 12, the user assigns the previously categorized images in step 9 to a task. Specifically, the user divides the captured images into essential and non-essential functions of a job. In one embodiment, the user creates a process for accommodating physical or cognitive deficits for return to work, ADA (Americans with Disabilities Act) accommodation strategies, risk reduction, or safety issue mitigation. In one embodiment, the division between essential and non-essential functions of a job can be visually reported format for employers, physicians, safety managers, case managers, or legal personnel. The visual clarification of essential and non-essential functions allows for faster decisions on accommodations, mitigation, or prioritization. After this step, the documentation process is complete.

In step 13A, the data storage is categorized. The Dictionary of Occupational Titles (DOT) calculations produce a category of work level. This level is then stored for the reporting process. Levels are calculated and confirmed to specified definitions within the system. It is a particular advantage of the present invention that the system uniquely calculates DOT levels based on mathematical criteria. In some embodiments, the DOT levels for physical demand can be defined as sedentary work, light work, medium work, heavy work, and very heavy work. It should be understood, that these categories may be changed or updated.

In one embodiment, sedentary work is defined as exerting up to 10 pounds of force occasionally and/or a negligible amount of force to lift, carry, push, pull, or otherwise move objects, including the human body. Sedentary work involves sitting most of the time, but may involve walking or standing for brief periods of time. Jobs are sedentary if walking and standing are required only occasionally and all other sedentary criteria are met.

In one embodiment, light work is defined as exerting up to 20 pounds of force occasionally, and/or up to 10 pounds of force frequently, and/or a negligible amount of force constantly to move objects. Physical demand requirements are in excess of those for sedentary work. Even though the weight lifted may be only a negligible amount, a job should be rated Light Work: (a) when it requires walking or standing to a significant degree; or (b) when it requires sitting most of the time but entails pushing and/or pulling of arm or leg controls; and/or (c) when the job requires working at a production rate pace entailing the constant pushing and/or pulling of materials even though the weight of those materials is negligible. It is important to note that the constant stress and strain of maintaining a production rate pace, especially in an industrial setting, can be and is physically demanding of a worker even though the amount of force exerted is negligible.

In one embodiment, medium work is defined as exerting 20 to 50 pounds of force occasionally, and/or 10 to 25 pounds of force frequently, and/or greater than negligible up to 10 pounds of force constantly to move objects. Physical demand requirements are in excess of those for light work.

In one embodiment, heavy work is defined as exerting 50 to 100 pounds of force occasionally, and/or 25 to 50 pounds of force frequently, and/or 10 to 20 pounds of force constantly to move objects. Physical demand requirements are in excess of those for medium Work.

In one embodiment, very heavy work is defined as exerting in excess of 100 pounds of force occasionally, and/or in excess of 50 pounds of force frequently, and/or in excess of 20 pounds of force constantly to move objects. Physical demand requirements are in excess of those for heavy work.

The frequencies of the aforementioned DOT levels described above were previously described above by the terms occasionally (or occasional), frequently (or frequent), and constantly or (constant), which can be defined as activity or condition exists up to $\frac{1}{3}$ of the time, $\frac{1}{3}$ to $\frac{2}{3}$ of the time, and more than $\frac{2}{3}$ of the time respectively. For instance, assuming an 8 hour work day, there are 28,800 seconds in the day. The frequency of a physical demand multiplied by the duration can determine which type of DOT level is required for a specific job. That is, the DOT level and physical demands reflects the estimated overall strength requirement of the job, representing the strength requirements which are considered to be important for average, successful work performance. Thus, if the frequency of a physical demand multiplied by the duration is: greater than or equal to 1 second and less than or equal to 9,504 seconds the result is occasional, greater than or equal to 9,505 seconds and less than or equal to 19,008 seconds the result is frequent, and greater than or equal to 19,009 seconds the result is constant.

In step 13B, the data calculations of step 13A are performed for each occurrence of physical demand. These calculations objectify, standardize, and clarify how the end user establishes calculated findings regarding the final report. Further, data calculations reduce error and standardize user report findings. Proprietary data calculations are established by peer reviewed literature and definitions. Standardization of calculations occurs for every user in the same way, which reduces error in reporting, while improving the capability to stand up legal scrutiny.

In step 13C, the video image is stored. Specifically, the individually selected images are categorized and tagged with specific components for reporting process, allowing the user to edit, clone, or revise the selections. Then, the images are embedded into final report formatting and attached to specific details in the final report.

In step 14, the final report is generated. The final report is a visually documented report including images, calculated results, recommendations, accommodations, tasks, locations, companies, job titles, DOT classifications, physical demand descriptions (postures, positions, lifting, reaching, handling, manipulation, transporting, environmental conditions, sensory conditions), physical demand levels by task, ergonomic risks/opportunities, EHS risks/opportunities, report dates, and evaluations.

In step 15, the report is stored in storage, such as a data repository 103 (FIG. 1). Specifically, a copy of each report is stored with a unique identifier in a Portable Document Format (PDF). This storage allows for later retrieval and future cloning of a report should the need arise. In one embodiment, the storage is cloud based as well known in the art. Likewise, in step 16, the report is integrated for retrial via external systems.

In step 17, the renewal notification is generated. Specifically, each year after the date of purchase of the system, an email notification will be sent to each user or company. This notification is a reminder that the reports completed need to be reviewed. In step 18, the renewal notice is sent. In step 19, if necessary the annual updates of a current or updated report are placed into data storage.

In step 20, the calculated data for Functional Testing Protocol (FTP) is extracted. This process allows the ability to take physical demand data collected and calculated to produce a functional testing protocol for post offer assessment testing and return to work testing. This data is called by external vending systems such as a Functional Capacity Evaluation (FCE) system to allow the two systems to communicate in the same language. This process results in the data for pre-hire post offer testing being specific to the physical demand data and visually captured reporting system. This is a particular advantage of the present invention as the system will be tested and integrated with WorkHab FCE Systems while image captures can now be used for specific task replication in the test development process.

In step 21, the functional testing report is generated. Integration and data extraction make it possible to connect physical demand job criteria and calculated demands directly with a functional capacity reporting system. This process results in accurate testing and reproducibility based on testing protocols and data gathered.

In step 22, the company information is setup. This process establishes company connection with their corresponding data that is collected and analyzed. It allows for reminders, system upgrades, functional test development, annually updating reports, cloning for similar facilities and tasks. The saves time and money for large companies.

In step 23, the company verification of final reports is completed. In this step, the company signs off and verifies each final report as a function of company management and legal liability protection. The signature and review of each final report both initially and annually keeps the company responsible for the information visually documented in each report.

In step 25, a clone report process is provided. Specifically, this process allows the user use an existing job or task to expedite the creation of a similar job or task at the same or new company. For instance, the user can clone an existing job, and then the change physical demands and video image captures to a new job. This process is also useful as an edit function.

In some embodiments, in step 40 each risk factor entered into the system is via body part and cycle time. In step 41, risk data and video captures are stored and sent to Odds Ratios data table. Next, in step 42, the body part data is summed to create job cycle outline task population. The system also checks to see if other standardized tests have been completed for one or more tasks in step 45. These are stored in risk assessment storage 46. In step 43, body part and task data are converted to active and non-active time (fatigue cycle). Next, in step 44, the user is enabled to visually see the rotation and building of jobs.

In step 26, a determination is made if FTP is required. Specifically, the user decides if they want to add FTP regarding the hiring or return to work process. If no, the method is complete. If yes, the process moves to step 27, where the physical demand report data is reviewed for critical demands and essential functions. In this process, the system captures critical physical demands of the existing job. In one embodiment, the weights, frequencies, distances are calculated to establish testing criteria, providing a reliable way to collect and produce baseline testing criteria. In step 28, the previously created testing protocols for use in future testing developments are stored in a database. In step 29, complete test protocols including instructions is used to create a report template. After collection and calculation of physical tests a template is completed to establish a cover sheet of testing with all associated test protocols for printing. In step 30, stored test protocols are added to the final report template, bringing together the templated materials into a single document. These results in a final testing protocol and validity criteria created. The employer can now test employees for the job prior to hire or as a return to work after injury/illness and know that the criteria established to create the test is valid and reliable. This document can be printed in step 31.

In step 32, the testing protocols are verified. Specifically, this additional step is taken by the employer to insure the testing is valid. Workers who currently perform the task are asked to take the functional test to validate the similarity to the work that they currently perform, to determine if the test an accurate representation of the job. If any corrections are necessary, they are corrected in step 33. In step 34, the final version is stored. In step 35, test providers are instructed in the testing process to ensure they trained successfully in protocols for each specific company using the system. In step 36, the testing protocols are available to the test providers. Finally in step 37, verification is provided that the testing protocols are not disqualifying a significant portion of a protected population based on employer results of testing, ensuring that the employer remains in compliance with ADA, EEOC and any pending case law related to testing protocols. If the testing protocols are verified the method is complete. If no, the method returns to step 32.

Referring again to FIG. 1, server 102 is the centralized computer making the system available to various employers, utilizing the system and method described herein for an epidemiological approach to musculoskeletal risk determination and prediction of ergonomic risks, physical demand performance levels, occupational health monitoring and environmental, health, safety & sustainability (EHS&S) modeling. Further, to avoid workplace injuries, potential lawsuits, negligence, and other issues, the system and method assures a process which is repeatable, trainable, and standardized ensuring compliance and accommodating physical or cognitive deficits for return to work, as well as ADA accommodation strategies, risk reduction, and safety issues.

Figure 3:
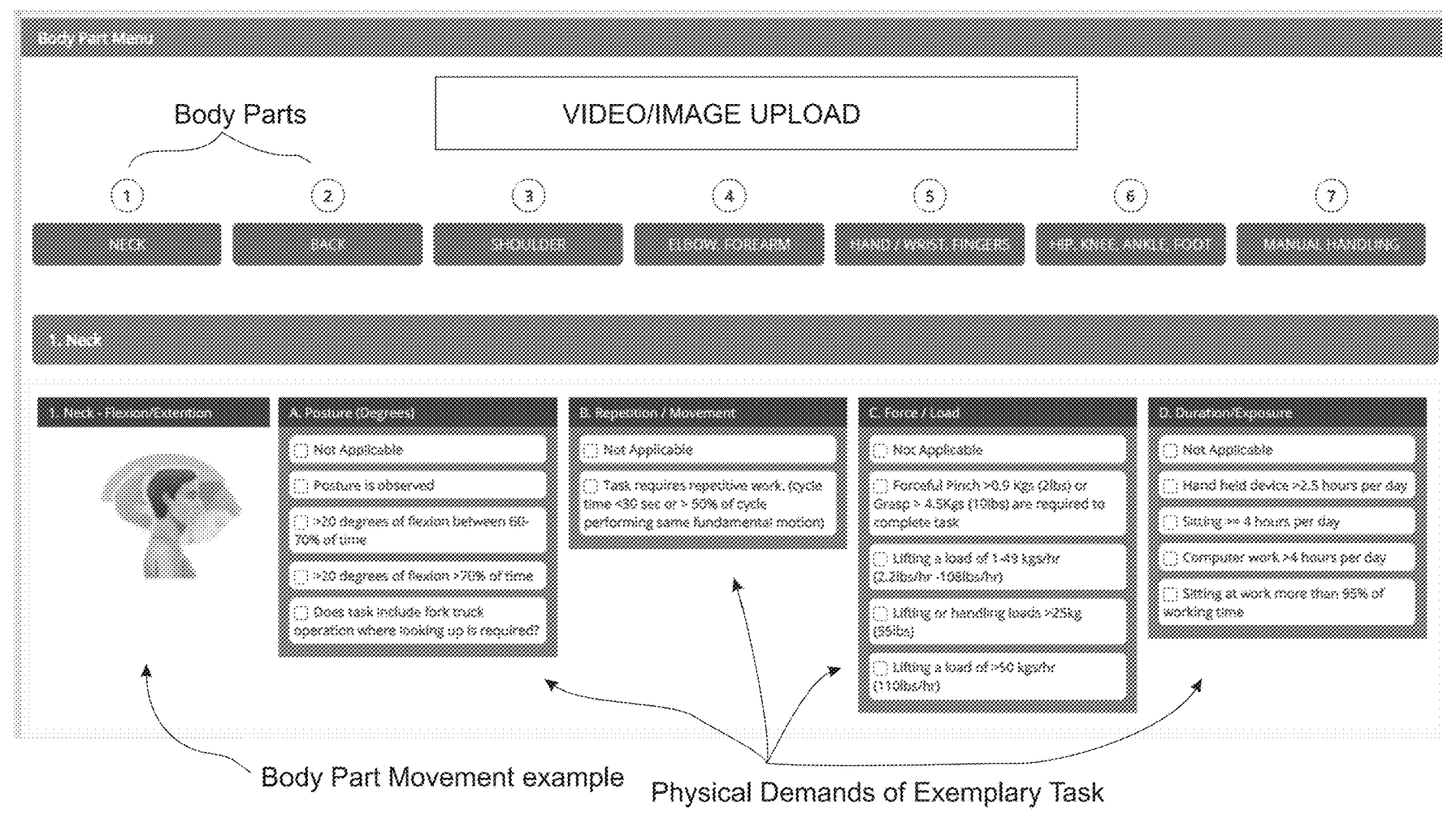

FIG. 3 is an exemplary user interface enabling a user to input a plurality of tasks by body part, and/or body part movements. In some embodiments, movements are broken down into right, left, or a combination thereof. This is a critical step for understanding actual job and task risk to perform analysis and determination of risk as described above. Inputs may be customized, prefilled options, ranges, etc.

Figure 4:
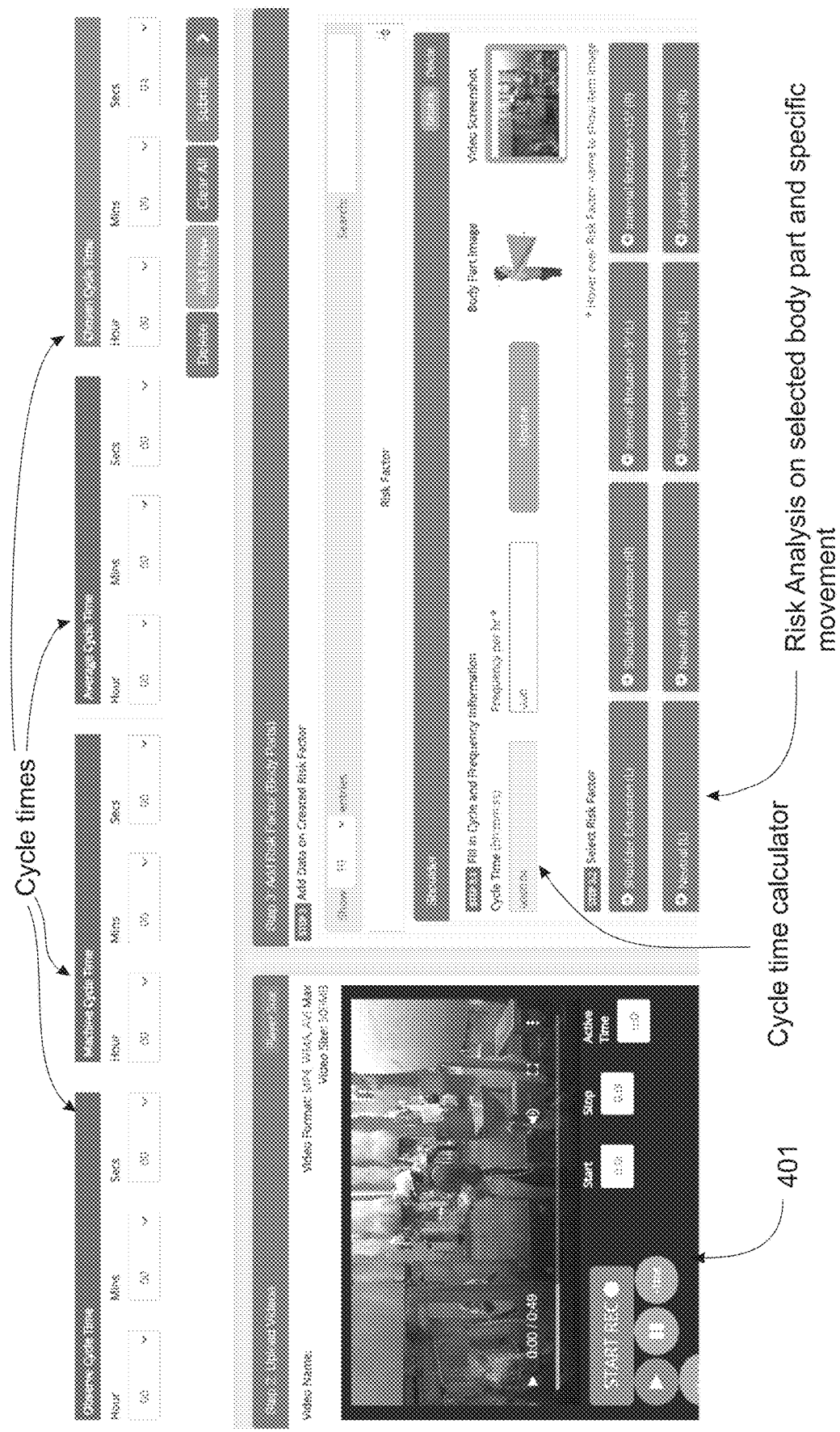
FIG. 4 is an exemplary user interface enabling a user to input and use physical demand data to create risk analysis according to an embodiment of the present invention.

FIG. 4 is an exemplary user interface enabling a user to input and use physical demand data to create risk analysis. In some embodiments, the shown user interface enables users to use risk analysis to begin building physical demand profiles, wherein each would operate as separate functions in the system. The captured images and/or videos 401 provide a visual aid to capture and document the physical demands. In some embodiments, built in cycle time calculators are configured assist the user in being accurate in the length of cycles.

Figure 5:
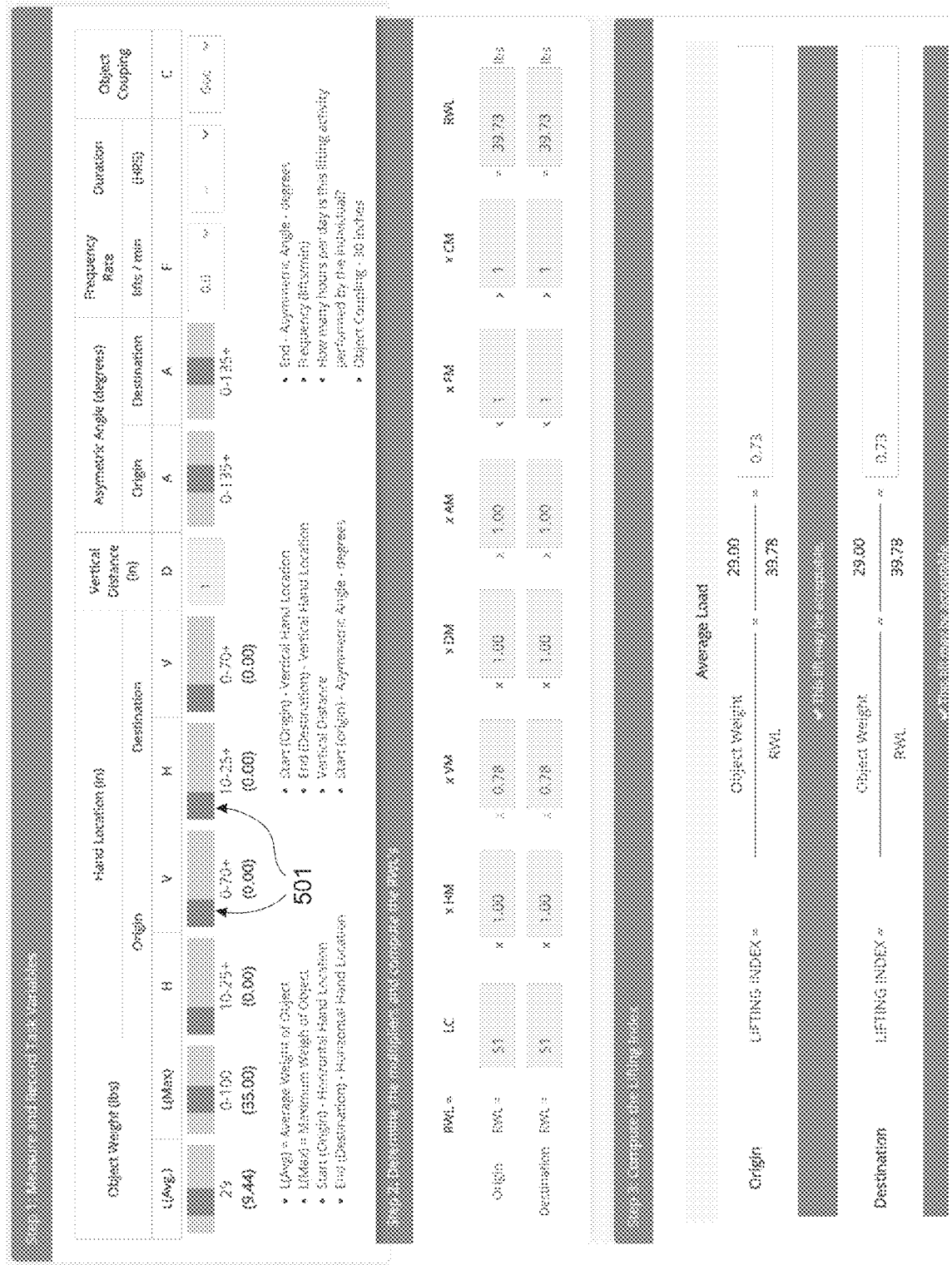
FIG. 5 is an exemplary user interface enabling a user to analyze data in various methods according to an embodiment of the present invention.

FIG. 5 is an exemplary user interface enabling a user to visually analyze data via sliding bars 501 to determine which components of lifting are creating the highest risk. Advantageously, this allows interactivity for the user and faster risk analysis for ergonomic teams. Also, this makes a determination if the lifts and/or tasks are acceptable according to National Institute for Occupational Safety and Health (NIOSH) Standards. In some embodiments, the system includes ability to calculated cumulative loads with comparison to odds ratio database and ISO recommendations, wherein the risk levels include cumulative carrying and the gender differentials via various lifts. In addition to lifts, similar functionality is also applied to push and pull movements.

Figure 6:
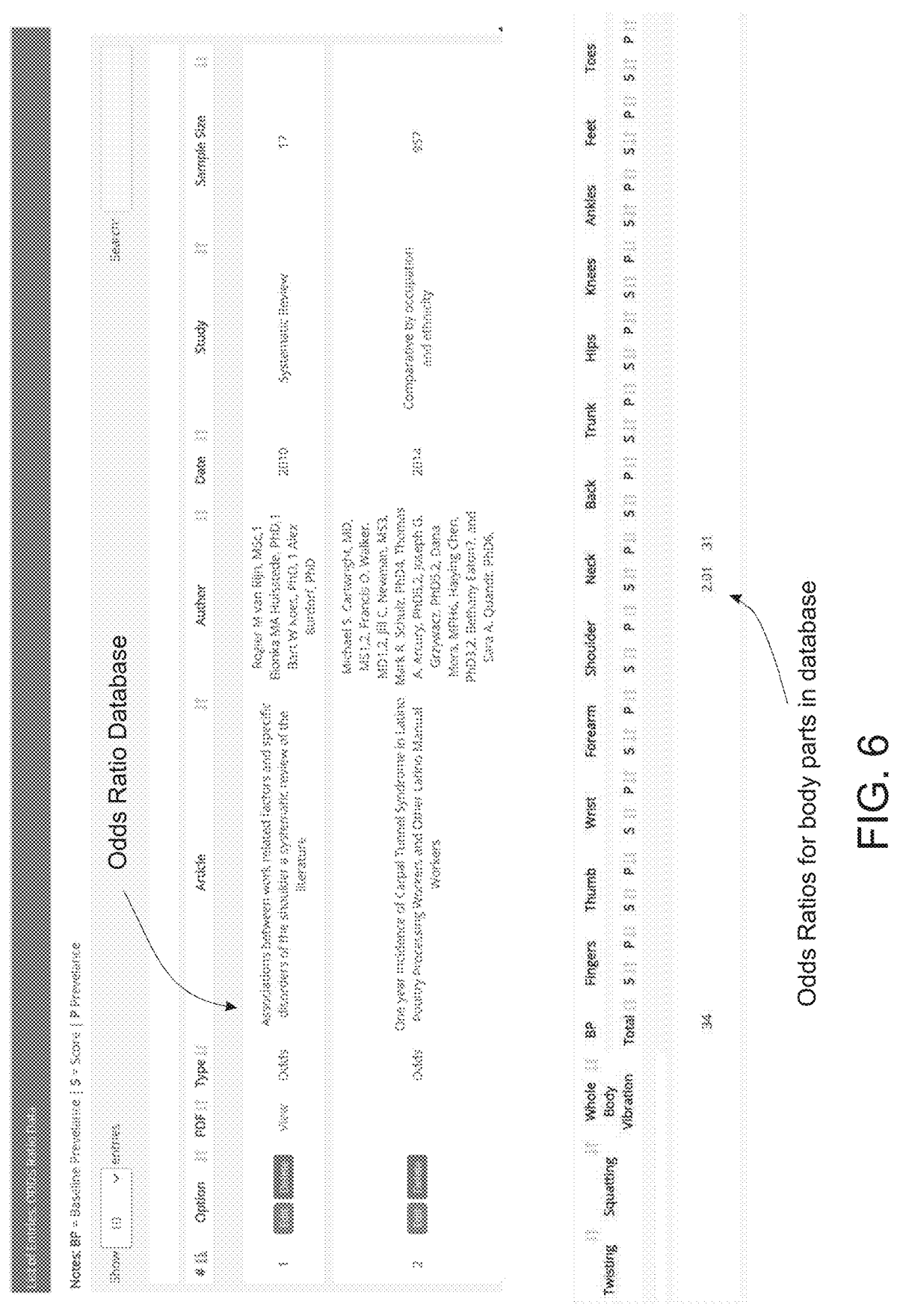

FIG. 6 shows an example results document based on the various input data, testing data, epidemiological data and occupational health data input into the system. A custom Odds Ratio epidemiological database is built into the system, which is used in the calculations of body part, task, and job risk. The results and data are updated as databases are updated with data ensuring risk data is up to date. Advantageously, the results may be displayed in various forms, including but not limited to bar graph, pie charts, line graphs, scatter plots, histograms, or other known displays of data. Also, the results may be focused for a variety of points or factors, including but not limited to body part, job, task, location of task, risks, cost etc. For example, the data may be focused on which risks are likely to create a medical claim based on the odds ratio.

Figure 7:
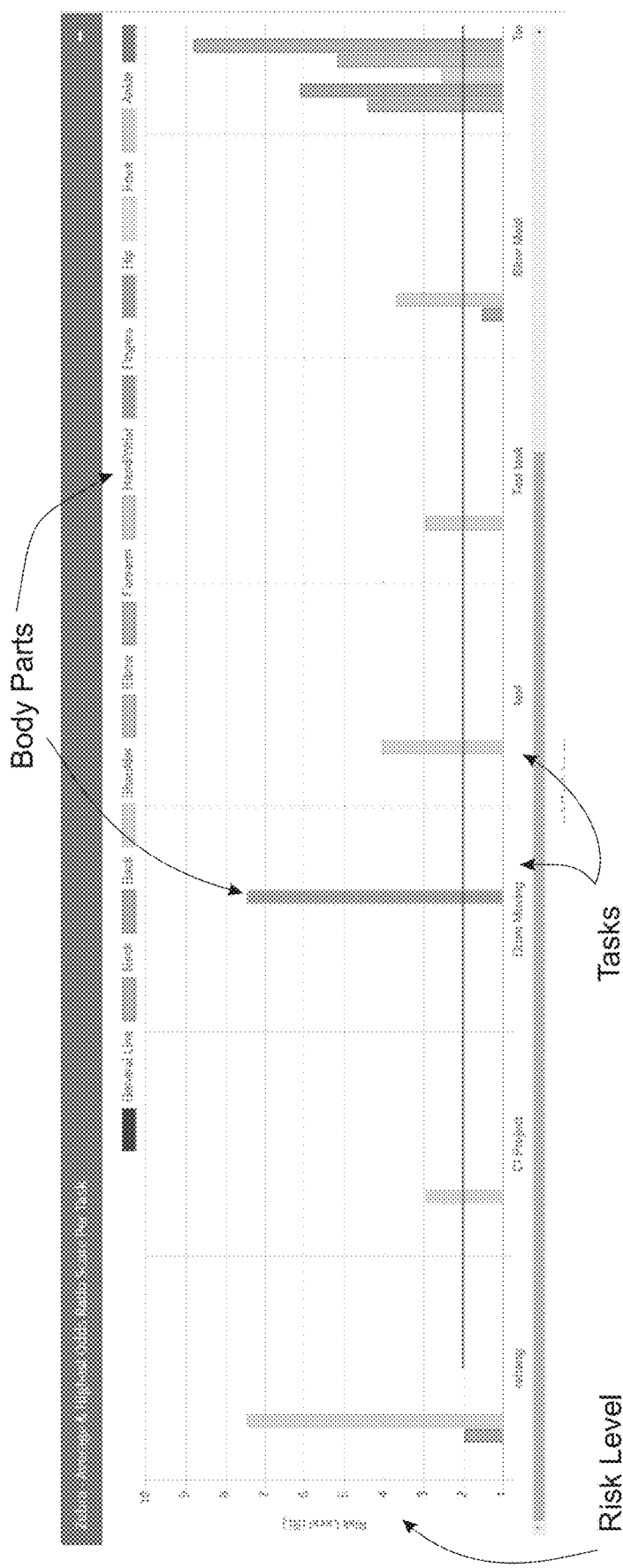
FIGS. 7-9 shows an example graphical risk analysis report based on the odds ratio and medical data inputted into the system according to an embodiment of the present invention.
Figure 8:
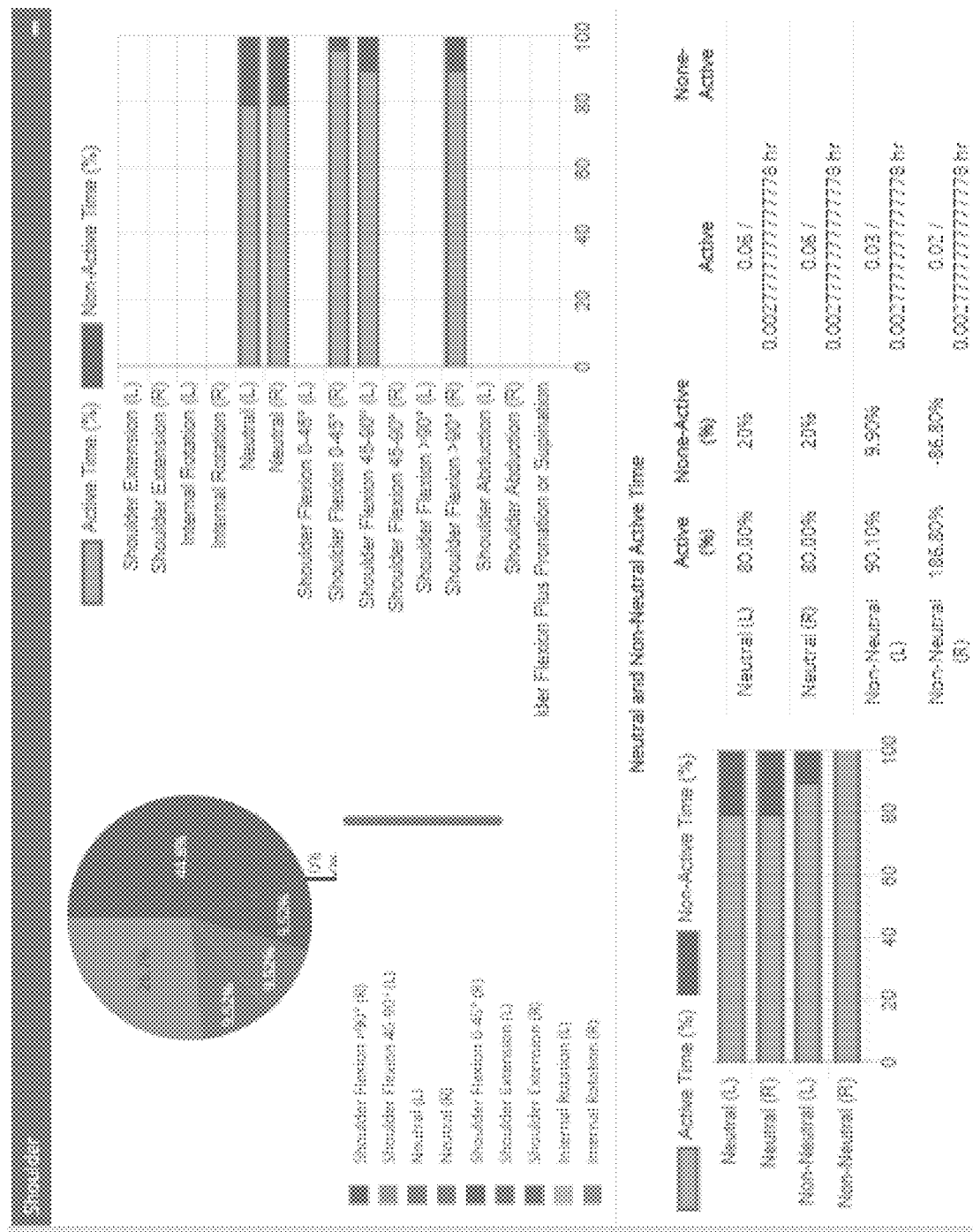
Figure 9:
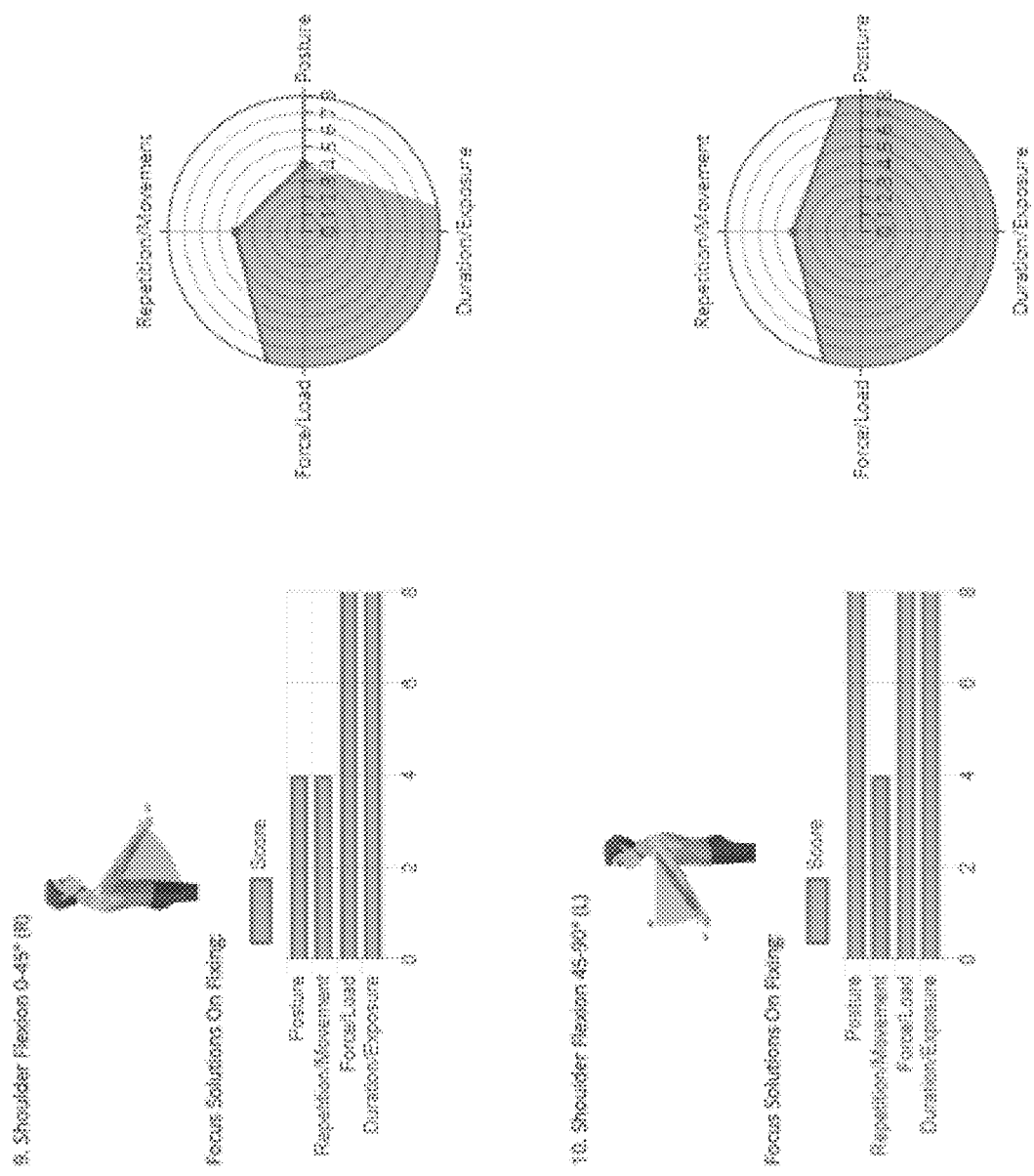

FIGS. 7-9 shows an example graphical risk analysis report based on the odds ratio and medical data inputted into the system. Advantageously, the report can illustrate to employers exactly the body part, job, task, location of task, line of risks and which is likely to create a medical claim based on the odds ratio. In some embodiments, radar graphs (FIG. 9) are provided to depict source of risks enable and allow the end user to quickly identify where to focus attention, dollars, and mitigation efforts. The reports can be customized and present in terms of risk level for tasks, body parts, movements, or other variables. Further, these reports include odds ratio based or epidemiological based triggers that are visually displayed for the end user to know where and when actions should be evaluated.

Figure 10:
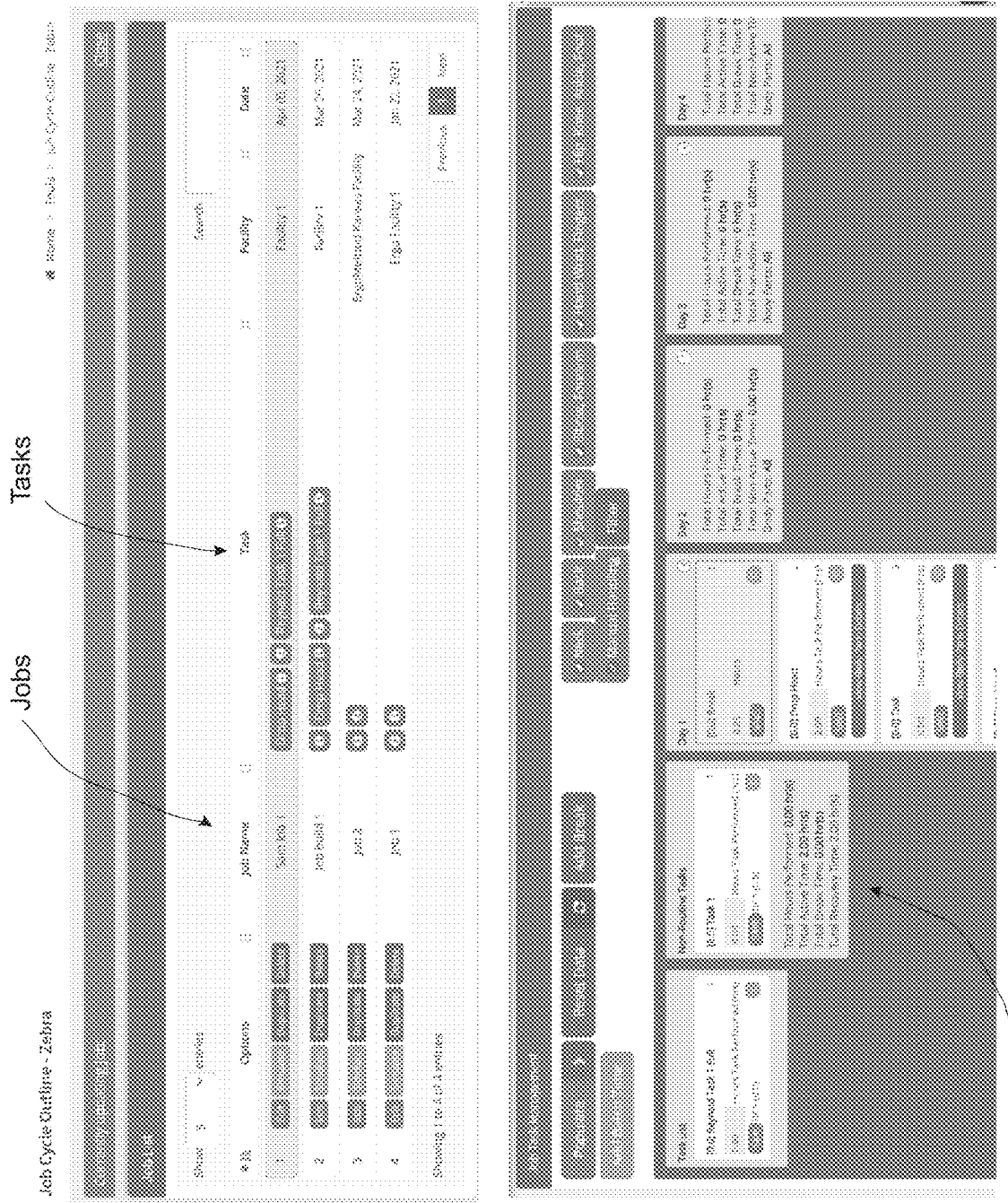
FIG. 10 shows an exemplary user interface of the system enabling a program for user review and interaction according to an embodiment of the present invention.

FIG. 10 shows an exemplary user interface of the system enabling a job cycle and rotation program for user review and interaction. Advantageously, a drop and drag feature is provide, visually showing how jobs can be rotated by task reviewing for risk factors and fatigue components. In some embodiments, interactive cards for each job task that can be placed on a day to build jobs by day including breaks and batch changes allowing more accurate risk determination (see "Schedule"). All tasks are then summarized to present a work day schedule which can then be used for scheduling or job rotation cycles. This factor's in total active time and total non-active time. In some embodiments, the system summarizes ISO fatigue data for end user to see if proper recover is occurring. In some embodiments, a fatigue function is provided, which allows the end user to review jobs lasting longer than the typical 8 hour day.

In some embodiments, the system offers many safety monitoring features for occupational health purposes. For example, in some embodiments modules are provided to discovery where safety and ergonomic risks may be trending or occurring. In some embodiments, this features a QR code driven tool that aids in building a safety culture where all employees can be involved. In another embodiment, COVID-19 tracking is provided, to keep track of supervisor alerts, temperature tracking, remote data entry, cleaning monitoring and quarantine tracking. FIG. 11 shows an exemplary instance of COVID-19 monitoring. In some embodiments, inspection lists or logs are provided for tracking and trending potential safety issues for compliance issues and machine safety. In some embodiments, this data is connected to the Odds Ratio database to allow safety professionals to understand the impact of the seemingly insignificant items on the overall safety and injury prevention program.

Figure 12:
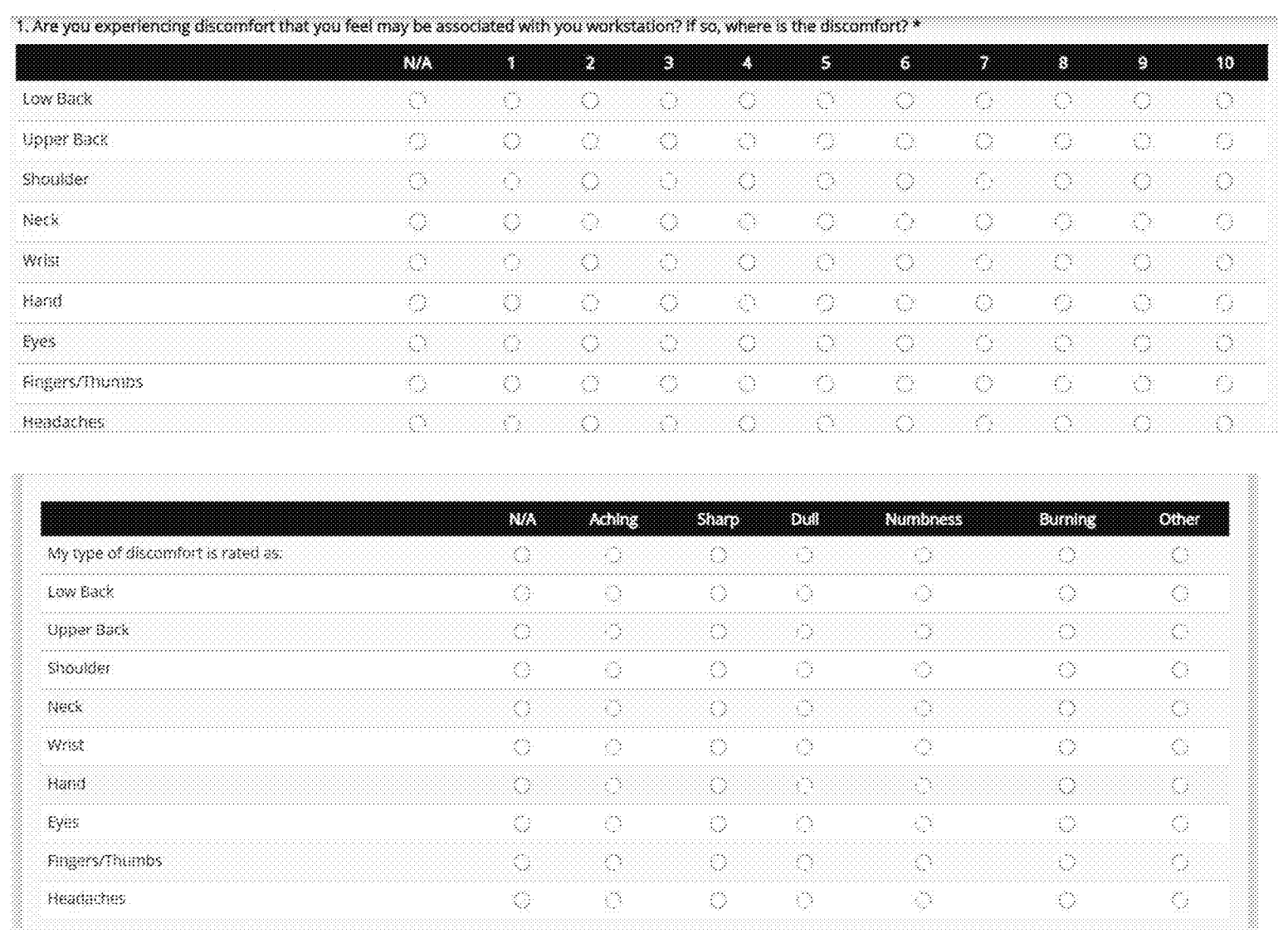

FIG. 12 shows an exemplary user interface of the system enabling self-assessment for ergonomic risk tracking. In some embodiments, the self-assessment includes a plurality of questions related to job tasks, and particular discomforts and/or pain for these job tasks as illustrated. The self-assessment provides the ability for office workstation, home, and remote area ergonomic assessments, as well as the ability to track and trend data, and alert supervisors for the need to review.

In some embodiments, the system provides goal setting and meeting tracking for ergonomic teams to manage goals and meetings within the system preventing having to enter the data into a separate spreadsheet. Meetings and projects are connected as well as managed through calendar functions to ensure projects stay on track.

It should be understood; that the system may be manipulated to factor in various state laws, such as worker's compensation law known as Rule 17 of Colorado. Any new laws may be added or adjusted by the system without departing from the scope and spirit of the invention.

Figure 13:
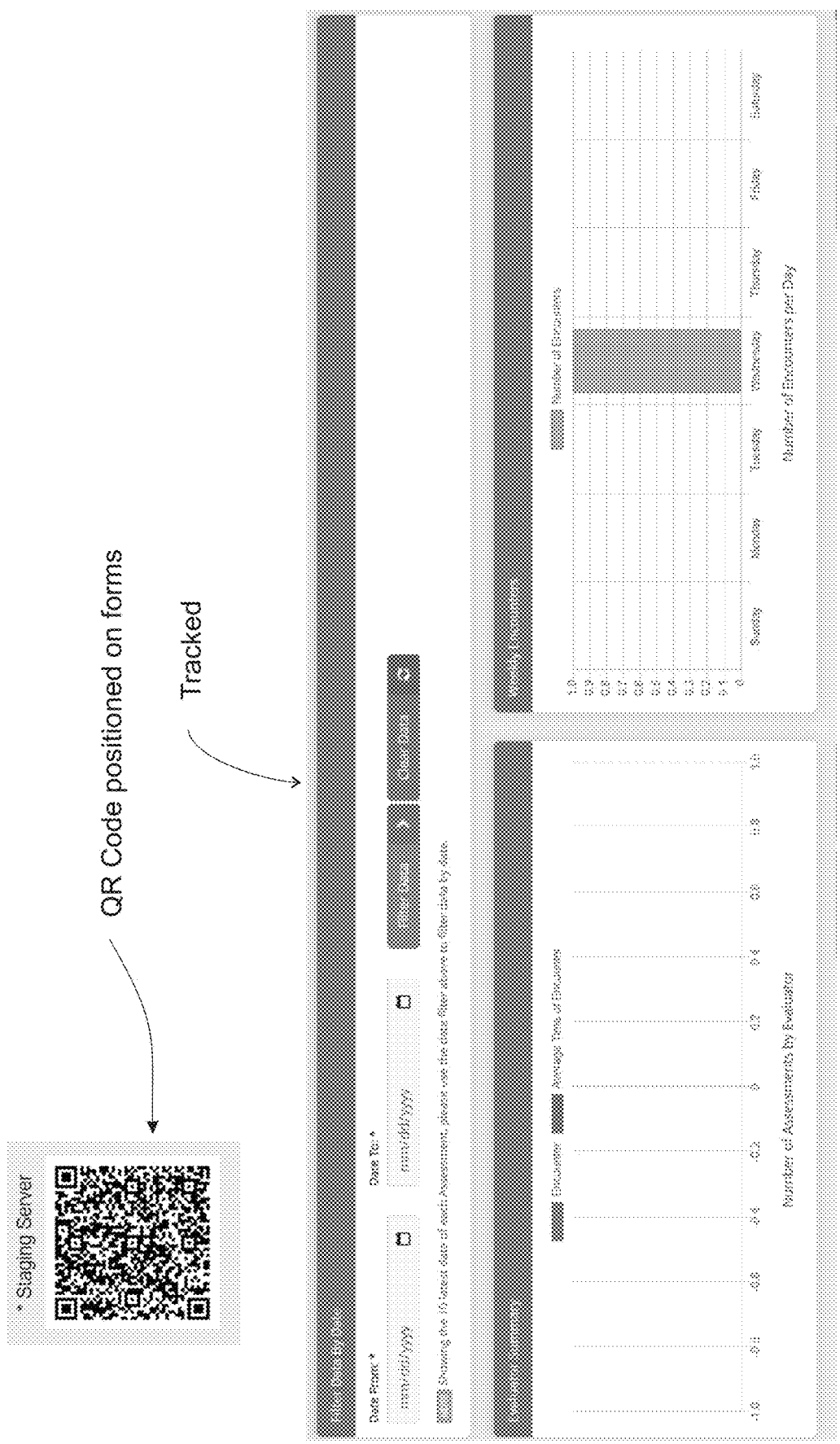
FIG. 13 shows an exemplary culture risk QR code integration tool according to an embodiment of the present invention.

FIG. 13 shows an exemplary culture risk integration tool. Culture has been demonstrated in the epidemiological literature to be one of the key factors in musculoskeletal injuries in the workplace. The system includes a unique tracking feature to make a more comprehensive solution for the end user. The system software can integrate QR coded forms to track and calculate different types of encounters with employees, management and vendors. These encounters can be tracked using a mobile device and a prebuilt question sampling. These can be used to review safety, ergonomic, lockout tag out, machine guarding, team involvement, management involvement, and facility competitions to track current group culture in a real-time format. In one embodiment, the Odds Ratio database includes the latest epidemiological data on how culture impacts safety, injury occurrence, injury duration, injury cost and how decision making by leadership can significantly reduce incidents thereby improving safety, quality and productivity. In some embodiments, the QR coded integrations can also be set to trigger safety responses so that safety personnel receive real-time notifications as soon as an event has occurred.

Advantageously, the system integrates evidence-based question-driven software logic that uses epidemiological data to calculate musculoskeletal risk based on body part known as ZEBRA. The system calculates "days at risk", "dollars at risk", and "dollars at risk by body part" based on severity rate calculations and normative injury data. The system uses Rstudio as a statistical calculation processor to ensure statistical measures so they are accurately presented in epidemiological formats. The system then provides ergonomic teams and management with solutions and recommendations table based on the types and severity of the risk. These include both administrative solutions and engineered solutions. The system provides ergonomic teams and management with real-time data dashboards containing information specific to the company's performance and status of evaluations, projects, engineered solutions, numbers and types of evaluations performed, list of subject matter experts trained, encounters performed, length of time of encounters and much more. In one embodiment, the system provides ergonomic teams and supervisors with a risk score based interactive line rotation functionality. In some embodiments, this can be used to lower risk scores by upper extremity, lower extremity, total score or manual handling risk score. In one embodiment, this uses a drop and drag of job tasks which then scores the risk based on rotation and length of recovery vs length of work cycle times. Additional key and unique components include built-in video-based training, integrated QR coding, occupational health first reporting, culture forms and encounter tracking, safety encounters, machine guarding assessment, rule 17 (Colorado specific tool), forensic and causation report program, and integration of in focus work applications software.

In some embodiments, various risk assessments generated by the system can be compared to predicted values. For example, predicted hand threshold activity levels published by the American Conference of Governmental Industrial Hygienists can be compared to the actual assessment generated from the user inputs as described above.

In some embodiments, the system includes embedded videos for teaching users how to use the specific tools and functionality of the system, for entering data to generating reports.

The system provides the ability to enter incident/injury reports such that they may track and factored into job tasks. In some embodiments, this is defined as an Occupational Health visit forms and tracking system which allows for tracking and trending of musculoskeletal injuries, the creation of individual at risk individuals, integration with the causation reporting system, and triggering mechanism for ergonomic risks or job tasks that are trending negatively. In some embodiments, the system is also HIPPA compatible by only allowing healthcare professionals access to medical related data that is not related to a workers job.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Although the invention has been described in considerable detail in language specific to structural features and or method acts, it is to be understood that the invention defined in the appended claims is not necessarily limited to the specific features or acts described. Rather, the specific features and acts are disclosed as exemplary preferred forms of implementing the claimed invention. Stated otherwise, it is to be understood that the phraseology and terminology employed herein, as well as the abstract, are for the purpose of description and should not be regarded as limiting. Therefore, while exemplary illustrative embodiments of the invention have been described, numerous variations and alternative embodiments will occur to those skilled in the art. Such variations and alternate embodiments are contemplated, and can be made without departing from the spirit and scope of the invention.

What is claimed is:

1. A system comprising:
   an Internet-connected computerized appliance having a processor and coupled to a data repository, the processor executing software from a non-transitory storage medium, the software providing an interactive health monitoring and musculoskeletal risk determination and prediction system, the system enabling a user to:
   log on;
   input detailed ergonomic and biomechanical data related to one or more body parts including posture, body movement tasks, and applied forces;
   capture and store media data to document physical demands and ergonomic risk corresponding to a plurality of tasks at a worksite;
   calculate and determine musculoskeletal and ergonomic risk factors based on the inputted data;
   utilize a specifically configured odds ratio database in the calculation and determination of the musculoskeletal and ergonomic risk factors based on statistical associations between observed ergonomic conditions and historical injury data;
   analyze the musculoskeletal and ergonomic risk factors; and,
   generate a plurality of reports detailing and illustrating the musculoskeletal and ergonomic risk factors including predictive analytics for injury prevention.

2. The system of claim 1, wherein the applied forces includes lifting movements, carry movements, push movements, and pull movements.

3. The system of claim 1, wherein the worksite is a home office.

4. The system of claim 1, wherein the system provides the integration and cross validation of standardized ergonomic risk assessment tools with the odds ratio data from the odds ratio database.

5. The system of claim 1, wherein the system provides the integration of fatigue ratio and fatigue systems to improve calculations of the musculoskeletal and ergonomic risk factors.

6. The system of claim 1, wherein the system provides a QR code tracking and monitoring system for occupational health and safety.

7. The system of claim 6, wherein the QR code tracking and monitoring system comprises Covid-19 data tracking, wherein the data tracking essentially consists of: temperature tracking, quarantine tracking, remote data entry, and cleaning monitoring.

8. The system of claim 6, wherein the QR code tracking and monitoring system wherein the occupational health and safety comprises job safety analysis, LOTO data, and customizable QR coding activities.

9. The system of claim 6, wherein the odds ratio data base integrates a solutions database to aid in calculations.

10. The system of claim 1, the system further enabling a user to: input additional data in a self-assessment module for ergonomic risk tracking.

11. The system of claim 1, the system further enabling a user to: drop and drag date specific task lists for the development of an effective job cycle for a period of time.

12. The system of claim 2, wherein the analysis of the musculoskeletal and ergonomic risk factors is via sliding bars to visually analyze the data to determine which components of lifting movements are creating the highest risk.

13. The system of claim 1, the system further enabling the user to: identity specific body parts affected by the physical demands.

14. The system of claim 8, the system further enabling the user to: create a body part based risk report based on potential injury cost.

15. A method comprising steps:
   (a) providing training and credentialing of a plurality of users for use of a worksite risk analysis and documentation system that utilizes statistical risk assessments based on an odds ratio database;
   (b) enabling a user of the plurality of users to access the worksite risk analysis and documentation system via an Internet connection to perform risk analysis from any geographical location;

(c) capturing media data at a worksite, wherein the media data includes video or images documenting specific physical demands and ergonomic risk of the user or an additional user;
(d) capturing ergonomic and biomechanical input data related to one or more body parts from the user, including posture, body movement tasks, and applied forces;
(e) storing the inputted data and captured media data in a non-transitory storage medium;
(f) calculating musculoskeletal and ergonomic risk factors using a specifically configured odds ratio database that correlates observed conditions with historical injury data based on the inputted data and captured media data;
(g) analyzing the musculoskeletal and ergonomic risk factors; and,
(h) generating a plurality of reports detailing and illustrating the musculoskeletal and ergonomic risk factors including predictive analytics for injury prevention.

16. The method of claim 15, wherein the applied forces includes lifting movements, carry movements, push movements, and pull movements.

17. The method of claim 15, wherein the plurality of reports includes a body part based risk report based on potential injury cost.

* * * * *